US00PP32429P2

(12) United States Plant Patent
Shafer

(10) Patent No.: US PP32,429 P2
(45) Date of Patent: Nov. 3, 2020

(54) ***SALVIA* PLANT NAMED 'WHITE FLAME'**

(50) Latin Name: ***Salvia* hybrid**
Varietal Denomination: White Flame

(71) Applicant: Ball Horticultural Company, West Chicago, IL (US)

(72) Inventor: Gail Shafer, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/873,290

(22) Filed: Mar. 11, 2020

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508
See application file for complete search history.

*Primary Examiner* — Anne Marie Grunberg
(74) *Attorney, Agent, or Firm* — Audrey Charles

(57) ABSTRACT

A new and distinct cultivar of *Salvia* plant named 'White Flame', characterized by its white-colored flowers, dark green-colored foliage, and vigorous, upright growth habit, is disclosed.

1 Drawing Sheet

Latin name of genus and species of plant claimed: *Salvia* hybrid.

Variety denomination: 'White Flame'.

BACKGROUND OF THE INVENTION

The present invention relates to a new and distinct cultivar of *Salvia* plant botanically known as *Salvia* hybrid and hereinafter referred to by the cultivar name 'White Flame'.

The new cultivar originated in a controlled breeding program in West Chicago during spring 2016. The objective of the breeding program was the development of a *Salvia* cultivar having vigorous, upright growth habits and long-lasting inflorescences for improved garden performance.

The new *Salvia* hybrid cultivar is the result of open-pollination. The female (seed) parent of the new cultivar is the proprietary *Salvia* hybrid breeding selection coded salvf-wh-A63-1, not patented, characterized by its characterized by its white-colored flowers, medium green-colored foliage, and vigorous, upright growth habit. The male (pollen) parent of the new cultivar is unknown. The new cultivar was selected as a single flowering plant within the progeny of the above stated open-pollination during June 2016 in a controlled environment in Arroyo Grande, Calif.

Asexual reproduction of the new cultivar by terminal stem cuttings since June 2016 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'White Flame' as a new and distinct cultivar of *Salvia* plant:

1. White-colored flowers;
2. Dark green-colored foliage; and
3. Vigorous, upright growth habit.

Plants of the new cultivar differ from plants of the female parent primarily in being taller and wider.

Of the many commercially available *Salvia* cultivars, the most similar in comparison to the new cultivar is 'Balsalmispim', U.S. Plant Pat. No. 29,604. However, in side by side comparisons, plants of the new cultivar differ from plants of 'Balsalmispim' in at least the following characteristics:

1. Plants of the new cultivar have inflorescences that often curve with age unlike plants of 'Balsalmispim';
2. Plants of the new cultivar have white colored flowers unlike plants of 'Balsalmispim'; and
3. Plants of the new cultivar have smaller sized corollas, as measured by width and depth, than plants of 'Balsalmispim'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'White Flame'. The approximately 3-month-old plants were grown in 6-inch pots for 7 weeks in a greenhouse in West Chicago, Ill. Plants were given one pinch two weeks before transplant.

DETAILED BOTANICAL DESCRIPTION

Figure 1:
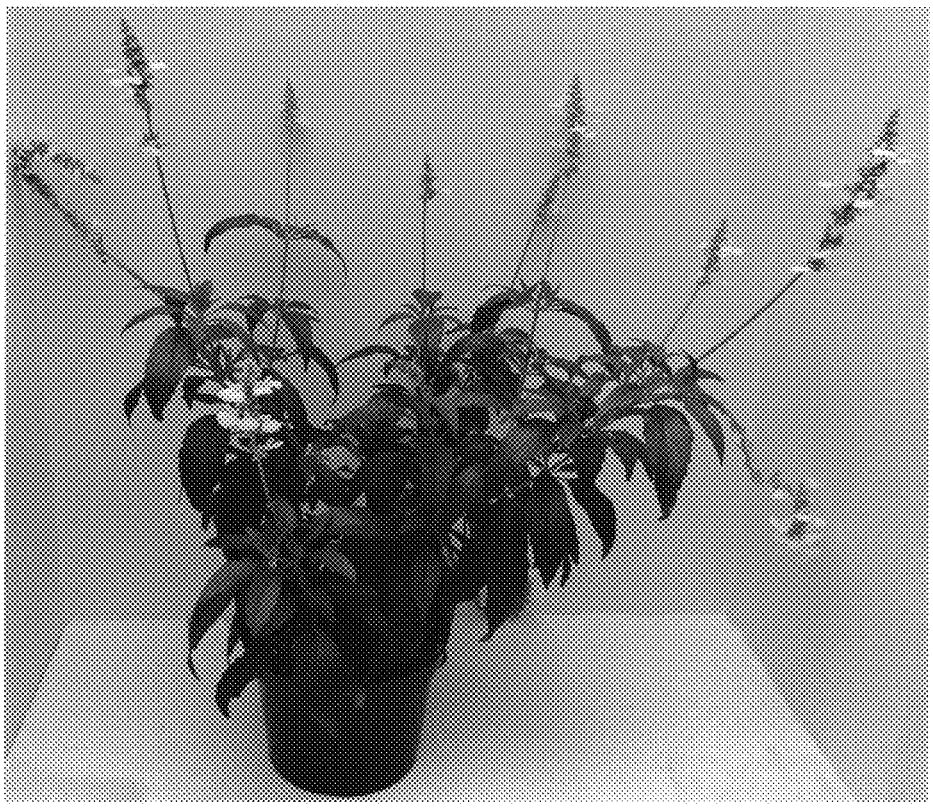
FIG. 1 illustrates a side view of the overall growth and flowering habit of 'White Flame'.
Figure 2:
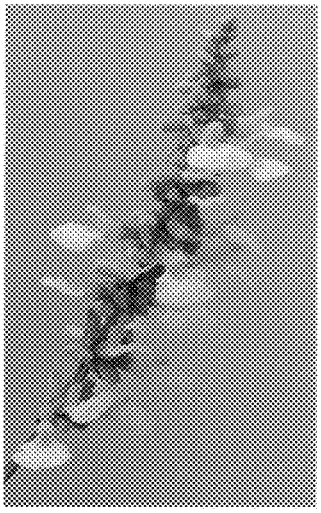
FIG. 2 illustrates a close-up view of an inflorescence of 'White Flame'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in December 2019 under natural light conditions in West Chicago, Ill.

The following descriptions and measurements describe approximately 3-month-old plants produced from cuttings from stock plants and grown in a glass-covered greenhouse under conditions comparable to those used in commercial practice. The plants were grown in West Chicago, Ill. in 6-inch pots for 7 weeks utilizing a soilless growth medium. Plants were given one pinch two weeks before transplant. Greenhouse temperatures were maintained at approximately 67° F. to 72° F. (19° C. to 22° C.) during the day and approximately 64° F. to 66° F. (18° C. to 19° C.) during the night. Supplemental lighting was used. Measurements and numerical values represent averages of typical plants.

Botanical classification: *Salvia* hybrid 'White Flame'.

Parentage:

*Female parent.*—salvf-wh-A63-1, not patented.

*Male parent.*—Unknown.

Propagation:

*Type cutting.*—Terminal stem.

*Time to initiate roots.*—Approximately 5 to 8 days.

*Time to produce a rooted cutting.*—Approximately 21 to 42 days.

*Root description.*—Fine, fibrous.

*Rooting habit.*—Freely branching.

Plant description:

*Commercial crop time.*—Approximately 6 to 10 weeks from a rooted cutting to finish in a 15 cm pot.

*Growth habit and general appearance.*—Annual, vigorous, upright growth habit.

*Size.*—Height from soil level to top of plant plane: Approximately 48.0 cm. Width: Approximately 43.0 cm.

*Branching habit.*—Freely branching. Pinching enhances lateral branching. Quantity of branches per plant: Approximately 2.

*Branch.*—Shape: Square in cross section. Strength: Strong. Length to base of inflorescence: Approximately 24.0 cm. Diameter: Approximately 4.0 mm. Length of central internode: Approximately 4.5 cm. Texture: Densely pubescent with short, appressed hairs. Color of young and mature stems: 146B, pubescence makes color appear lighter.

Foliage description:

*General description.*—Quantity of leaves per main branch: Approximately 6 to 8. Fragrance: Slight, sage-like. Form: Simple. Arrangement: Opposite.

*Leaves.*—Aspect: Petiole acute to perpendicular angle to stem, leaf blade becomes obtuse angle with age. Shape: Ovate. Margin: Crenate. Apex: Acute. Base: Obtuse. Venation pattern: Pinnate. Length of mature leaf: Approximately 9.0 cm. Width of mature leaf: Approximately 3.0 cm. Texture of upper surface: Moderately pubescent with short, fine hairs. Texture of lower surface: Densely pubescent on venation only. Color of upper surface of young and mature foliage: 137A with 139A and venation of 146D. Color of lower surface of young and mature foliage: Closest to 137B with venation of 146D.

*Petiole.*—Length: Approximately 2.5 cm. Diameter: Approximately 2.0 mm. Texture: Densely pubescent. Color: 146D.

Flowering description:

*Flowering habit.*—'White Flame' is freely flowering under outdoor growing conditions with substantially continuous blooming from spring through autumn and year-round in greenhouse environment.

*Lastingness of individual floret.*—Approximately 4 to 5 days.

Inflorescence description:

*General description.*—Type: Spikes in verticillaster arrangement, florets in clusters of nine, not persistent, often curved with age. Quantity of inflorescences per plant: Approximately 13. Fragrance: Faint, sweet. Length or height of inflorescence: Approximately 11.0 cm. Width of inflorescence: Approximately 4.0 cm. Quantity of fully-open flowers per inflorescence: Approximately 66, two to three per cluster open at one time.

*Peduncle.*—Shape: Square in cross section. Strength: Strong. Aspect: Erect. Length: Approximately 8.0 cm to 15.0 cm. Diameter: Approximately 3.0 mm. Texture: Densely pubescent with short, appressed hairs. Color: 146B, color appears lighter due to pubescence.

Flower description:

*Type.*—Single, zygomorphic.

*Bud.*—Rate of opening: Generally takes 2 to 3 days for bud to progress from first color to fully open flower.

*Bud just before opening.*—Shape: Obovoid. Length: Approximately 8.0 mm. Diameter: Approximately 3.0 mm. Texture: Densely pubescent. Color: Calyx of 144A, color appears lighter due to pubescence, and petal portion of 157D.

*Corolla.*—Shape: Bilabiate, lower lip having three lobes, base fused. Width: Approximately 1.2 cm. Length: Approximately 1.0 cm. Depth: Approximately 2.0 cm.

*Upper lip.*—Shape: Hooded. Margin: Entire. Apex: Rounded. Length from throat: Approximately 5.0 mm. Width: Approximately 4.0 mm. Texture of inner surface: Glabrous. Texture of outer surface: Densely pubescent. Color of pubescence: NN155D. Color of inner and outer surface when first and fully open: NN155D.

*Lower lip.*—Shape of central lobe: Obovate. Margin: Entire. Apex of central lobe: Emarginate. Apex of lateral lobes: Rounded. Length from throat of central lobe: Approximately 1.0 cm. Width of central lobe: Approximately 1.2 cm. Length from throat of lateral lobes: Approximately 5.0 mm. Width of lateral lobes: Approximately 2.0 mm. Texture of upper surface: Glabrous. Texture of lower surface: Sparsely pubescent. Color of upper and lower surface when first and fully open: NN155D.

*Corolla tube.*—Length: Approximately 1.0 cm. Diameter at opening: Approximately 2.0 mm. Diameter at base: Approximately 1.0 mm. Texture of inner and outer surfaces: Glabrous. Color of inner and outer surface when first and fully open: NN155D.

*Calyx.*—Shape: Tubular. Length: Approximately 7.0 mm. Diameter: Approximately 4.0 mm.

*Sepals.*—Quantity per flower: Fused into two lobes. Shape: Obovate. Apex: Upper lobe acute, lower lobe notched. Length: Approximately 7.0 mm. Width of lobes: Approximately 4.0 mm. Texture of inner surface: Glabrous. Texture of outer surface: Densely pubescent. Color of inner surface: 144A. Color of outer surface: 144A, color appears lighter due to pubescence.

*Bracts.*—Quantity: One bract located at the base of each floret cluster. Length: Approximately 2.0 mm. Width: Approximately 1.0 mm. Texture of inner surface: Glabrous. Texture of outer surface: Densely pubescent. Color of inner surface: 144A. Color of outer surface: 144A, color appears lighter due to pubescence.

*Pedicel.*—Strength: Strong, flexible. Aspect: At an acute angle. Length: Approximately 1.0 mm. Diameter: Approximately 0.5 mm. Texture: Densely pubescent. Color: 144A, color appears lighter due to pubescence.

*Reproductive organs.*—Androecium: Stamen quantity: 2 per flower, dorsifixed, strongly curved. Stamen length: Approximately 8.0 mm. Filament length: Approximately 7.0 mm. Filament color: NN155D, opaque. Anther shape: Oblong. Anther length: Approximately 1.0 mm. Anther color: 12C transitioning to N199D at dehiscence. Pollen amount: Abundant. Pollen color: 12C. Gynoecium: Pistil quantity: 1 per flower. Pistil length: Approximately 1.3 cm. Stigma shape: Cleft, two-parted. Stigma length: 2.0 mm. Stigma color: NN155D. Style length: Approximately 9.0 mm. Style color: NN155D, opaque. Style texture: Glabrous with a vertical line of feather-like pubescence of NN155D extending from the stigma for approximately 6.0 mm. Ovary length: Approximately 2.0 mm. Ovary color: 154D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'White Flame', substantially as herein illustrated and described.

* * * * *